(12) United States Patent
Kinoshita et al.

(10) Patent No.: US 9,107,777 B2
(45) Date of Patent: Aug. 18, 2015

(54) DISPOSABLE WEARING ARTICLE

(75) Inventors: Akiyoshi Kinoshita, Kanonji (JP); Maiko Suzuki, Kanoji (JP); Kazuya Fujimoto, Kanonji (JP); Yusuke Kawakami, Kanonji (JP); Makoto Ichikawa, Kanonji (JP); Nobuhiro Tagawa, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 117 days.

(21) Appl. No.: 14/001,772

(22) PCT Filed: Feb. 28, 2012

(86) PCT No.: PCT/JP2012/001358
§ 371 (c)(1),
(2), (4) Date: Aug. 27, 2013

(87) PCT Pub. No.: WO2012/117723
PCT Pub. Date: Sep. 7, 2012

(65) Prior Publication Data
US 2013/0338623 A1    Dec. 19, 2013

(30) Foreign Application Priority Data

Feb. 28, 2011 (JP) .................. 2011-043367
Feb. 27, 2012 (JP) .................. 2012-040762

(51) Int. Cl.
*A61F 13/496*    (2006.01)
*A61F 13/49*    (2006.01)

(52) U.S. Cl.
CPC ......... *A61F 13/49011* (2013.01); *A61F 13/496* (2013.01)

(58) Field of Classification Search
CPC ............ A61F 2013/49025; A61F 2013/49026; A61F 2013/49028; A61F 2013/49033; A61F 13/49009; A61F 13/4902

USPC ............ 604/385.24, 385.25, 385.26, 385.27, 604/385.28, 385.29, 385.3
See application file for complete search history.

(56) References Cited

U.S. PATENT DOCUMENTS

2001/0049516 A1    12/2001  Shimada et al.
2005/0080394 A1    4/2005   Otsubo et al.
(Continued)

FOREIGN PATENT DOCUMENTS

EP    2186495 A1    5/2010
JP    2001333932 A   12/2001
(Continued)

OTHER PUBLICATIONS

Written Opinion of the International Searching Authority mailed Jun. 5, 2012 in corresponding International Application No. PCT/JP2012/001358 filed Feb. 28, 2012.
(Continued)

*Primary Examiner* — Tan-Uyen (Jackie) T Ho
*Assistant Examiner* — Peter S Vasat
(74) *Attorney, Agent, or Firm* — Lowe Hauptman & Ham, LLP

(57) ABSTRACT

Embodiments of this invention provide a disposable wearing article facilitating even an aged person having relatively weak forth to pull a waist-opening periphery in the transverse direction to widen the waist-opening to a desired size, despite this and the waist region should not slip down during use of the wearing article. Waist elastic elements (36) are stretched in the transverse direction X at a stretch ratio in a range of about 2.5 to about 3.0 and having fineness in a range of about 800 to about 1000 dtex, a dimension between the waist elastic elements (36) adjacent in the transverse direction X is in a range of about 5.5 to about 6.0 mm and each of waist elastic regions (38) in which the waist elastic elements (36) are present has a tensile stress at a moment of 255% stretching in the transverse direction X in a range of about 4.5 to about 6.0N/35 mm and a tensile stress at a moment of 167% stretching in the transverse direction is in a range of about 1.7 to about 2.1N/35 mm.

11 Claims, 9 Drawing Sheets

(56) References Cited

U.S. PATENT DOCUMENTS

| | | |
|---|---|---|
| 2005/0148988 A1 | 7/2005 | Kinoshita et al. |
| 2006/0042746 A1 | 3/2006 | Ukegawa |
| 2007/0208317 A1* | 9/2007 | Krautkramer et al. ..... 604/385.3 |

FOREIGN PATENT DOCUMENTS

| | | | |
|---|---|---|---|
| JP | 2003290279 A | 10/2003 | |
| JP | 2005095574 A | 4/2005 | |
| JP | 2006095277 A | 4/2006 | |

OTHER PUBLICATIONS

Corresponding International Application No. PCT/JP2012/001358 Search Report dated Jun. 5, 2012.

Extended European Search Report dated May 28, 2015, corresponding to European patent application No. 11828749.9.

* cited by examiner

DISPOSABLE WEARING ARTICLE

TECHNICAL FIELD

This disclosure relates to disposable wearing articles, and more particularly, to disposable wearing articles for adults.

BACKGROUND

Disposable wearing articles are known to be provided in the front and rear waist regions with a plurality of waist elastic elements extending in the circumferential direction. For example, JP 2003-290279 A (PTL 1) discloses a disposable wearing article provided in front and rear waist regions of a chassis of the wearing article with a plurality of waist elastic elements spaced one from another in a longitudinal direction of the chassis and extending in a transverse direction.

CITATION LIST

Patent Literature

{PTL 1} JP 2003-290279 A

SUMMARY

Technical Problem

In the disposable wearing article disclosed in PTL 1, a circumferential dimension of the front and rear waist regions is twice or more the length dimension of the front and rear waist regions in the longitudinal direction. In consequence, a waist-opening periphery can be widened around the wearer's waist to put the wearing article on the wearer's body and putting the wearing article on the wearer's body is correspondingly facilitated. In addition, the waist elastic elements may be arranged closely in given portions of the front and rear waist regions to enhance the body fit and thereby to prevent the wearing article from slipping down along the wearer's body during use of the wearing article.

However, in the wearing article having a relatively wide dimension in the circumferential direction of the waist, the inventors have recognized that it is required to provide the waist-opening periphery with the waist elastic elements having a relatively high tensile stress. To satisfy this requirement, flat rubber bands having a predetermined width dimension may be appropriately utilized in such a type of wearing articles. However, such flat rubber bands might excessively tighten the wearer's waist and leave pressure traces on the wearer's skin or create a feeling of discomfort against the wearer. Particularly when the wearer is an aged person, the wearer could feel difficult to sufficiently pull the waist-opening periphery in the transverse direction to widen the waist-opening fully and might be forced to spend time and effort to put the wearing article on the body.

Solution to Problem

According to some embodiments of this invention, there is provided a disposable wearing article having a longitudinal direction and a transverse direction being orthogonal to the longitudinal direction, including a chassis having a skin-facing side, a non-skin-facing side, a front waist region, a rear waist region and a crotch region extending between the front and rear waist regions, and a liquid-absorbent structure extending across the crotch region into the front and rear waist regions.

This invention resides in that the chassis has an inner sheet lying on the skin-facing side and an outer sheet lying on the non-skin-facing side;

the article further includes waist elastic elements sandwiched between the inner and outer sheets to extend along a waist-opening periphery of the chassis in the transverse direction;

the waist elastic elements are bonded to the chassis while being stretched in the transverse direction at a stretch ratio in a range of about 2.5 to about 3.0 and have fineness in a range of about 800 to about 1000 dtex;

a spacing dimension between the waist elastic elements adjacent in the longitudinal direction is in a range of about 5.5 to about 6.0 mm; and an annular waist elastic region in which the waist elastic elements are present has a tensile stress at 255% elongation in the transverse direction in a range of about 4.5 to about 6.0N/35 mm and a tensile stress at 167% elongation in the transverse direction in a range of about 1.7 to about 2.1N/35 mm.

DESCRIPTION OF EMBODIMENTS

Figure 1:
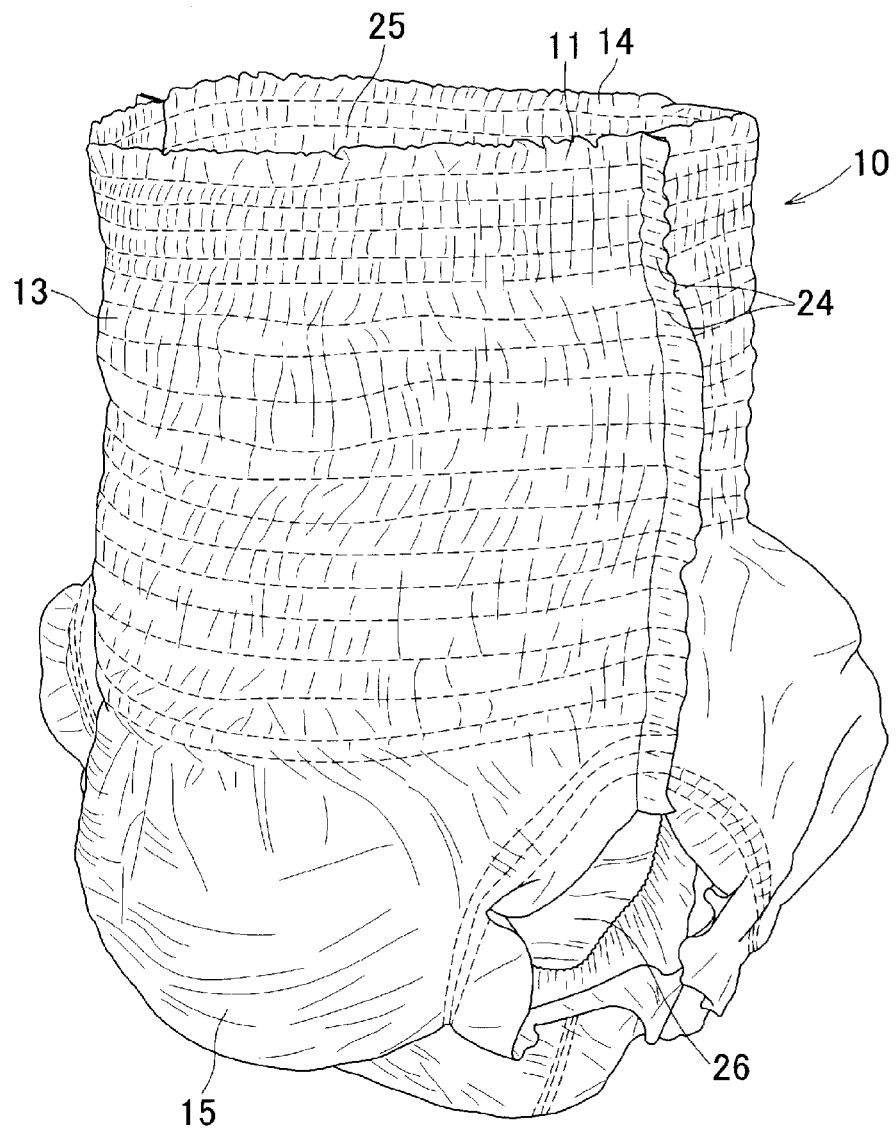
FIG. 1 is a perspective view of a disposable diaper as an example of the disposable wearing article according to one or more embodiments of the present invention.
Figure 2:
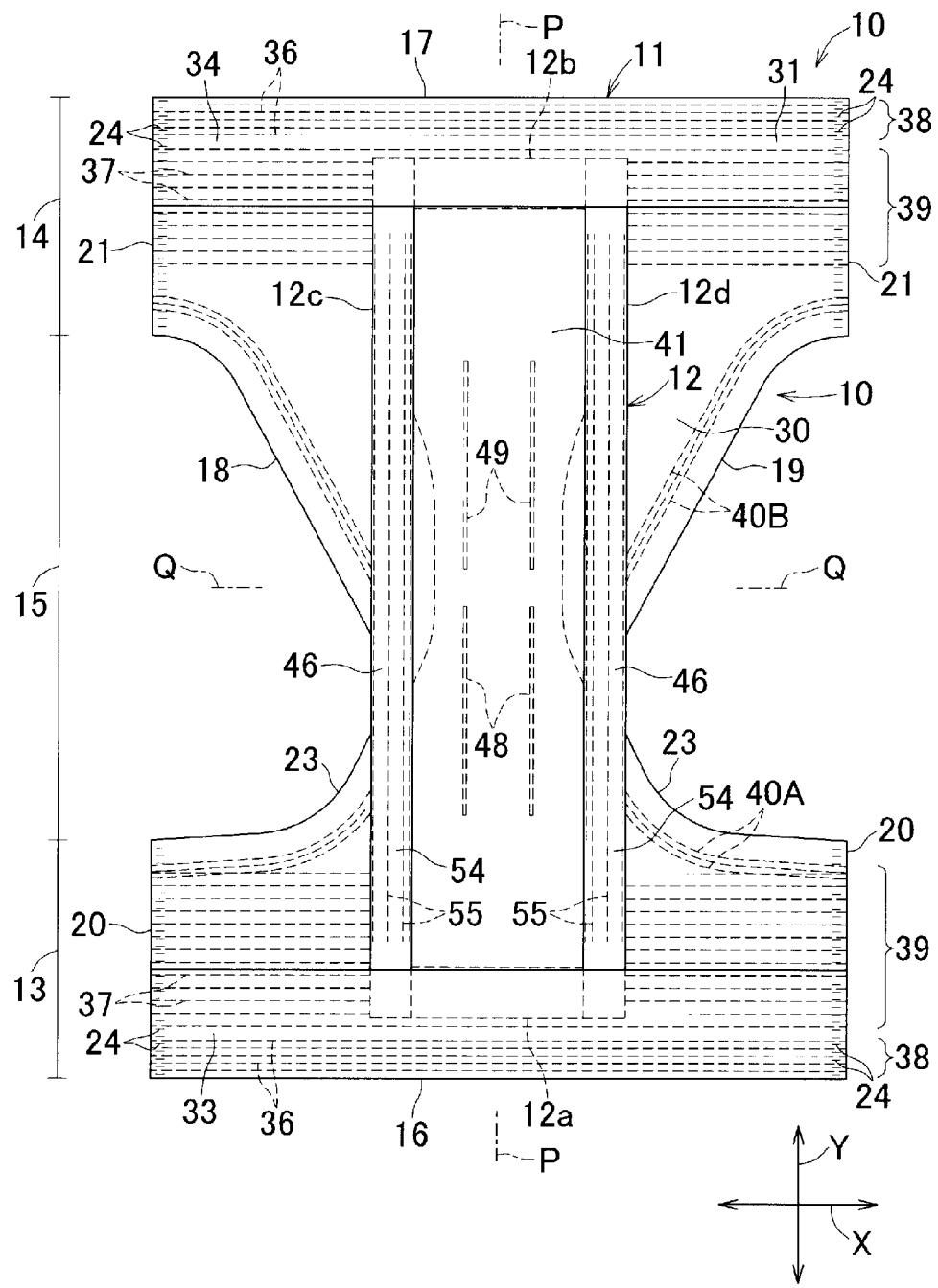
FIG. 2 is a partially cutaway unfolded plan view of the diaper of FIG. 1 having been developed in a front-back direction after side seams have been released and as viewed from the inner surface of the diaper.
Figure 3:
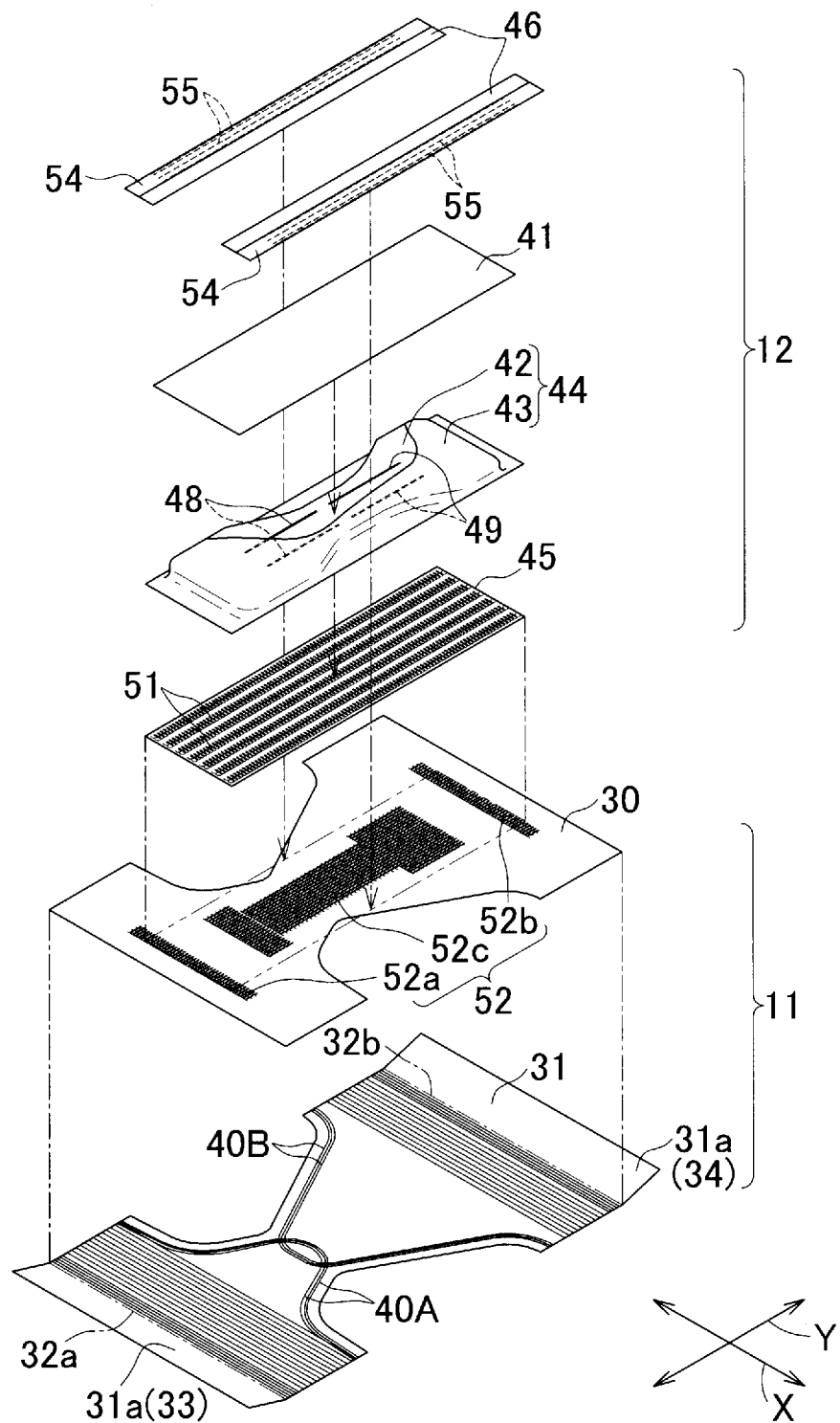
FIG. 3 is an exploded perspective view of the diaper of FIG. 1.

Referring to FIGS. 1 through 3, a disposable diaper 10 has a longitudinal axis P-P, a transverse axis Q-Q being orthogonal to the longitudinal axis P-P, a longitudinal direction Y extending along the longitudinal axis P-P, a transverse direction X extending along the transverse axis Q-Q, and includes a skin-facing side, a non-skin-facing side, and a chassis 11 defining an outer layer of the diaper 10 and a liquid-absorbent structure 12 lying on the skin-facing side of the chassis.

The chassis 11 has a front waist region 13, a rear waist region 14, a crotch region 15 located between the front and rear waist regions 13, 14, front and rear ends 16, 17 opposed to each other in the longitudinal direction Y and extending in the transverse direction X, and side edges 18, 19 opposed to each other in the transverse direction X and extending in the longitudinal direction Y. The side edges 18, 19 respectively include a pair of front and rear waist region's side edges 20, 21, and crotch region's side edges 23 concavely extending between these front and rear regions' side edges 20, 21 to fit to the wearer's thighs. The front and rear waist region's side edges 20, 21 are coupled with each other by side seams 24 arranged intermittently in the longitudinal direction Y to define a waist-opening 25 and a pair of leg-openings 26 (See FIG. 1).

The chassis 11 includes an inner sheet 30 including a moisture-pervious fibrous nonwoven fabric or the like and lying on the skin-facing side and an outer sheet 31 having a length dimension in the longitudinal direction Y larger than that of the inner sheet 30 and lying on the non-skin-facing side. The outer sheet 31 extends outwards in the longitudinal direction Y beyond the front and rear ends and these extensions 31a are folded inward along front and rear fold lines 32a, 32b (corresponding to the front and rear ends of the front and rear waist regions, respectively) extending in the transverse direction X along the front and rear ends of the inner sheet 30 to form front and rear flaps 33, 34.

As a pants-type disposable diaper for an adult, particularly for an aged person, a specific length dimension measured between the front and rear ends 16, 17 of the diaper 10 in the longitudinal direction Y is in a range of about 750 to about 850 mm and, more specifically, is about 780 mm. A length dimension measured between the front waist region's opposite side edges 20 and between the rear waist region's opposite side edges 21 in the transverse direction X, respectively, is in a range of about 450 to about 750 mm and, more specifically, is about 550 mm. It should be appreciated that these dimensions are values measured with respective waist elastic elements to be described later being stretched against contractile strength thereof.

The inner and outer sheets 30, 31 may include various types of liquid-impervious fibrous nonwoven fabrics, for example, a spunbond nonwoven fabric, a point-bonded nonwoven fabric, an SMS (spunbond/meltblown/spunbond) nonwoven fabric, a liquid-impervious plastic film or a laminate thereof each having a basis mass in a range of about 10 to about 40 $g/m^2$, preferably in a range of about 10 to about 20 $g/m^2$. Specifically, the inner sheet 30 may be formed from an SMS nonwoven fabric having a basis mass in a range of about 10 to 25 $g/m^2$ and the outer sheet 31 may be formed from a spunbond nonwoven fabric having a basis mass in a range of about 15 to 25 $g/m^2$ to provide desired tensile stress in first and/or second waist elastic regions 38, 39 as described herein below.

Between the inner and outer sheet 30, 31, one or more first waist elastic elements 36 (e.g., thread, strand or string elastics) are interposed to extend along the front and rear ends 16, 17 of the front and rear waist regions 13, 14, respectively, in the transverse direction X. Between the respective first waist elastic elements 36 and the crotch region's side edges 23, one or more second waist elastic elements 37 (e.g., thread, strand or string elastics) are respectively arranged to extend in the transverse direction X. The first and second waist elastic elements 36, 37 are contractibly secured under tension in the transverse direction X with hot melt adhesive between the inner and outer sheets 30, 31 as described later. The first and second waist elastic elements 36, 37 serve to elasticize the front and rear waist regions 13, 14 of the chassis 11 at least in the transverse direction X so that a region in which the first waist elastic elements 36 are arranged defines a first waist elastic region 38 which is annular around the waist-opening 25, and a region in which the second waist elastic elements 37 are arranged defines a second waist elastic region 39 which is also annular. The second waist elastic region 39 and the first waist elastic region 38 extending along the waist-opening periphery are provided with the thread, strand or string elastics so that these regions may be elastically stretchable and contractible. Compared to the case in which these regions are provided with flat bands, an area over which the thread, strand or string elastics (e.g., rubber materials) press the wearer's skin as well as application area of adhesive used to secure rubber materials can be reduced and, consequently, the first and second waist elastic regions 38, 39 are soft and flexible. Considering that the aged person is apt to suffer from pressure traces left by the rubber materials on the skin, it is preferred that the waist-opening periphery has such soft and flexible texture.

Between the inner and outer sheets 30, 31, front leg elastic elements 40A convexly extending from the front waist region 13 toward the transverse axis Q-Q and rear leg elastic elements 40B convexly extending forward from the rear waist region 15 beyond the transverse axis Q-Q are interposed. The front and rear leg elastic elements 40A, 40B, in a zone of the crotch region between the front waist region 13 and the transverse axis Q-Q, are contractibly secured under tension in the transverse direction X with hot melt adhesive (not shown) between the inner and outer sheets 30, 31.

The front and rear leg elastic elements 40A, 40B may include one or more threads or flat rubber bands, for example, elastic threads each having fineness in a range of about 700 to about 850 dtex and stretch ratio in a range of about 1.5 to about 2.5. The front and rear leg elastic elements 40A, 40B provided to extend along the crotch region's side edges 23 elasticize the leg-openings' peripheries so that these leg-opening's peripheries may fit to the wearer's inguinal regions and thereby help prevent body waste from leaking beyond the leg-openings' peripheries. Particularly, the arrangement such that the front and rear leg elastic elements 40A, 40B intersect (FIG. 3) in the zone of the crotch region 15 between the front waist region 13 and the transverse axis Q-Q is effective to help prevent urine from sideway-leakage.

The liquid-absorbent structure 12 has a generally rectangular shape contoured by front and rear ends 12a, 12b and opposite side edges 12c, 12d being orthogonal to the front and rear ends 12a, 12b to extend across the crotch region 15 into the front and rear waist regions 13, 14 and includes a liquid-pervious bodyside liner 41, a liquid-absorbent core assembly 44 including a liquid-absorbent core 42 wrapped with a liquid-dispersant sheet 43 such as tissue paper, and a backing sheet 45 covering an entire lower surface of the liquid-absorbent core assembly 44. The bodyside liner 41 includes a pair of containment sheets 46 attached to its skin-facing side to extend in the longitudinal direction Y.

The bodyside liner 41 may include various types of liquid-pervious fibrous nonwoven fabrics, for example, an air-through fibrous nonwoven fabric having a basis mass in a range of about 16 to about 26 $g/m^2$, or a perforated plastic film or a laminate thereof.

The liquid-absorbent core 42 is formed by molding a mixture of fluff wood pulp fibers and superabsorbent polymer particles (SAP) and optionally thermoplastic fibers into a desired shape and has a basis mass in a range of about 400 to about 900 $g/m^2$. The liquid-absorbent core assembly 44 is formed with a pair of front compressed grooves 48 and a pair of rear compressed grooves 49 extending in the longitudinal direction Y and spaced apart from each other in the transverse direction X. These front and rear pairs of compressed grooves 48, 49 help prevent the liquid-absorbent core 42 from assuming an irregular shape and facilitate the liquid-absorbent structure 12 to curve along the front and rear pairs of compressed grooves 48, 49 and thereby to improve fit to the wearer's body.

The backing sheet 45 may include, for example, a moisture-pervious and liquid-impervious plastic film, a hydrophobic nonwoven fabric or a laminate thereof. If it is desired to use nonwoven fabrics, such as an SMS fibrous nonwoven fabric, a spunbond fibrous nonwoven fabric or the like having a basis mass in a range of 10 to about 30 g/m² may be used for the backing sheet 45. If it is desired to compose the backing sheet 45 of a plastic film, a specific type of plastic film having a basis mass in a range of about 15 to about 23 g/m² and a tensile strength value (as measured in accordance with JIS K-7127) in a range of about 8 to about 14N/25 mm in the longitudinal direction Y and in a range of about 1 to about 5.5N/25 mm in the transverse direction X may be used. To help prevent stuffiness within the diaper 10, the backing sheet 45 preferably should have a moisture vapor permeability value in a range of about 2200 to about 3800 g/m² per 24 hrs.

The backing sheet 45 is bonded to the lower surface of the liquid-absorbent core assembly 44 with a plurality of bonding lines 51 hot melt adhesive applied in a spiral pattern and extending in the longitudinal direction Y. The backing sheet 45 is bonded also to the skin-facing side of the inner sheet 30 with an inner bond zone 52 defined by coating the inner sheet 30 with hot melt adhesive. Specifically, the inner bond zone 52 includes front and rear bond zones 52*a*, 52*b* extending in the transverse direction X along the front and rear ends 16, 17 of the front and rear waist regions 13, 14, respectively, and a central bond zone 52*c* extending across the crotch region 15 in the longitudinal direction Y between the front and rear bond zones 52*a*, 52*b*. In this way, the backing sheet 45 has its upper surface partially bonded to the non-skin-facing side of the liquid-absorbent core assembly 44 with the bonding lines 51 and partially bonded to the skin-facing side of the inner sheet 30 with the bond zone 52. Compared to the arrangement in which both the upper and lower surfaces of a sheet member are fully bonded to other, opposing sheet members or the like, the backing sheet 45 according this embodiment can assure a high moisture permeability and can effectively help prevent the inside of the diaper 10 from becoming stuffy.

The containment sheets 46 may include a liquid-impervious SMS (spunbond/meltblown/spunbond) fibrous nonwoven fabric, a spunbond fibrous nonwoven fabric, a plastic sheet made of polyethylene or a laminate thereof, each having a basis mass in a range of about 10 to about 30 g/m². In each of the containment sheets 46, a single sheet layer may be turned up or two or more sheet layers may be layered one on another to form a sleeve 54 within which a cuff elastic element 55 (e.g., a thread, strand or string elastic) is arranged. During use of the diaper 10, such sleeve 54 is spaced apart upward from the bodyside liner 41 under contraction of the cuff elastic element 55 to form a barrier adapted to help prevent body waste from sideway-leakage.

Referring to FIG. 2, the front and rear ends 12*a*, 12*b* of the liquid-absorbent structure 12 are covered with the front and rear flaps 33, 34 of the chassis 11, respectively. Such an arrangement helps prevent, bodily fluids seeping through the front and rear ends 12*a*, 12*b* of the liquid-absorbent structure 12 from further leaking outward and soiling the wearer's garment.

Figure 4:
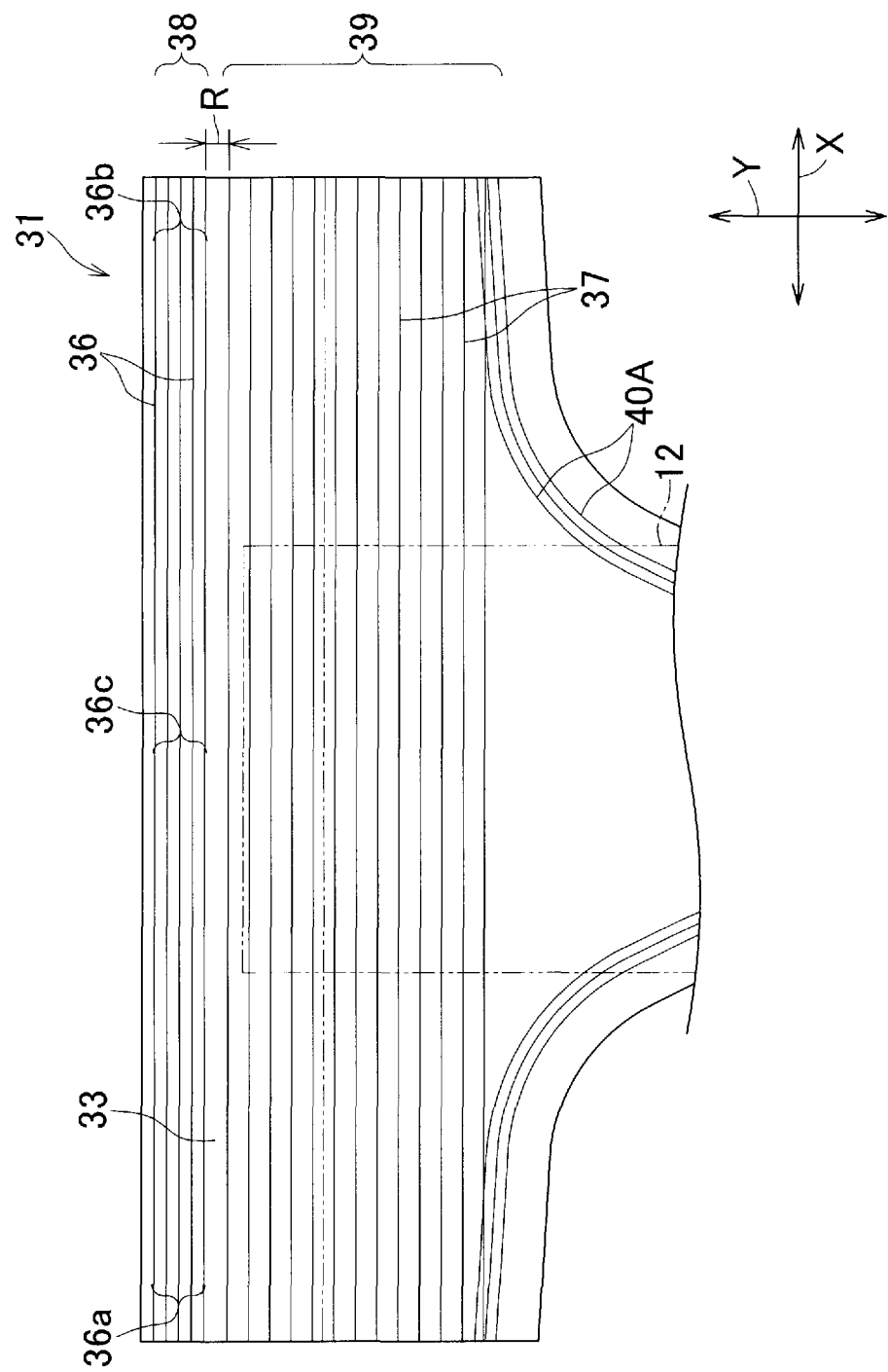
FIG. 4 is a scale-enlarged plan view of an area of an outer sheet defining a front waist region of the diaper of FIG. 1 with an inner sheet having been removed from a chassis.

Referring to FIG. 4, the liquid-absorbent structure 12 and the front flap 33 are indicated by imaginary lines. As has previously been described, the first and second waist elastic elements 36, 37 are interposed between the inner and outer sheets 30, 31 cooperating together to define the chassis 11 to compose the first and second waist elastic regions 38, 39. The first waist elastic elements 36 may include two or more elastic threads each having fineness in a range of about 800 to about 1000 dtex, a stretch ratio in a range of about 2.5 to about 3.0, and a spacing dimension (pitch) in the longitudinal direction Y in a range of about 5.5 to about 6.0 mm. The term "spacing dimension" used herein means a center-to-center distance between the adjacent waist elastic elements in the longitudinal direction Y. It should be understood that the term "pitch" used hereinafter in this specification is also defined in the same manner. The stretch ratio of about 2.5 to about 3.0 means that the waist elastic elements 36 are stretched to about 2.5 to about 3.0 times their natural lengths while being bonded to the chassis, e.g., the inner and/or outer sheet(s) 30, 31.

The second waist elastic elements 37 may also include two or more elastic threads (elastic material) similarly to the first waist elastic elements 36 each having fineness in a range of about 700 to about 1000 dtex, a stretch ratio in a range of about 1.8 to about 3.0, and a spacing dimension in the longitudinal direction Y in a range of about 8.0 to about 12.0 mm. A spacing dimension R between the innermost first waist elastic element 36 and the outermost second waist elastic element 37 in the longitudinal direction Y is in a range of about 8.0 to about 15.0 mm, preferably in a range of about 10.0 to about 12.0 mm.

Now the first waist elastic elements 36 will be described in more detail. For the first waist elastic elements 36, LYCRA 940 DTEX manufactured by TORAY OPERLONTEX CO., LTD. may be used. Tensile stress (as measured by Tensile Tester manufactured by Instron Japan Co., Ltd. to be described later) of each individual one of these elastic threads is in a range of about 0.3 to about 0.6N, more specifically, in a range of about 0.45 to about 0.55N in a state of being stretched to 255% (i.e., at 255% elongation) from a non-stretched state (i.e., 100%). Each individual elastic thread also has tensile stress in a range of about 0.2 to about 0.4N, more specifically, in a range of about 0.3 to about 0.36N in a state of being stretched to 255% (i.e., at 255% elongation) in the course of contracting after having been stretched more than 255%.

Figure 5:
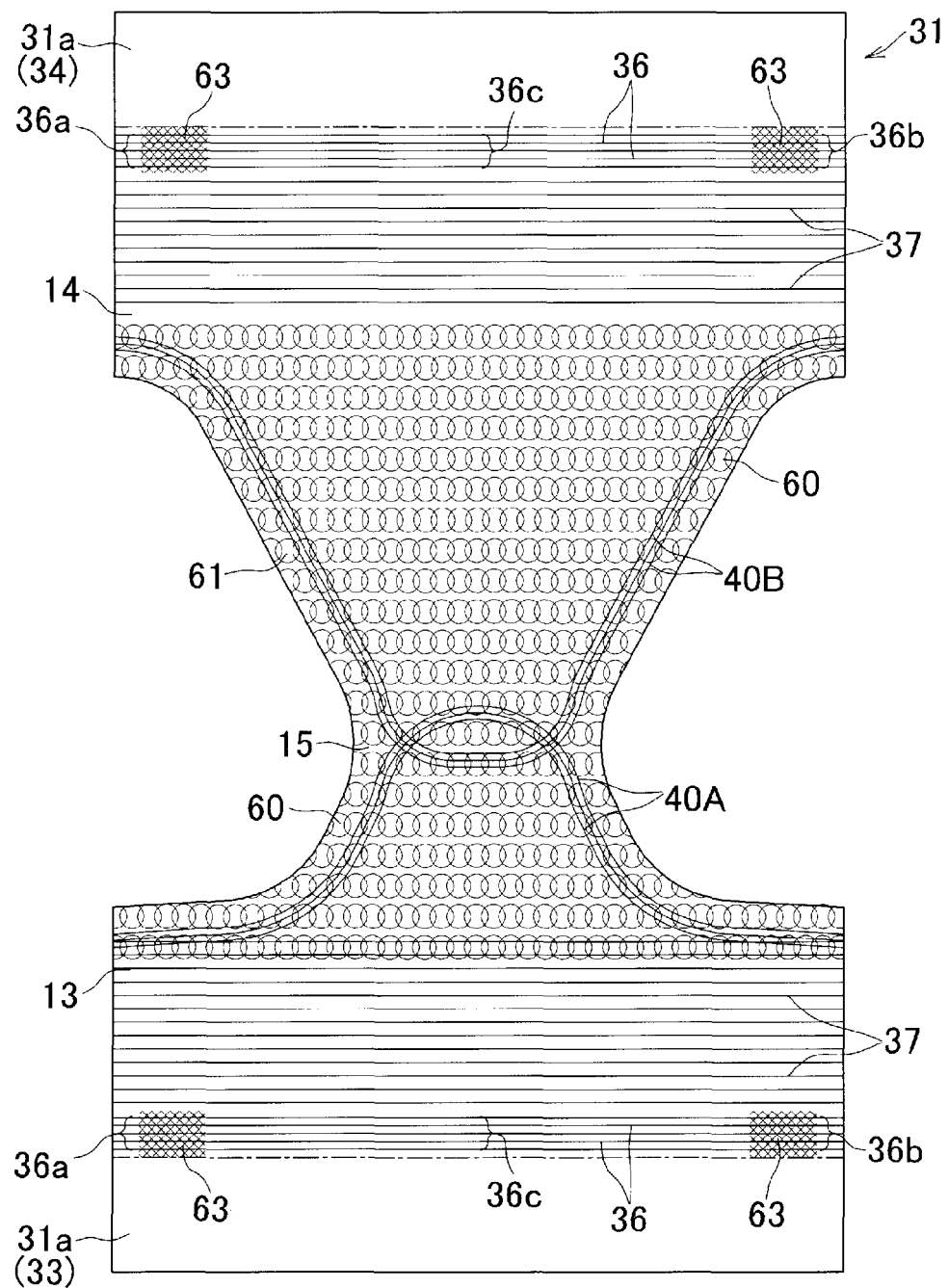
FIG. 5 is a plan view of an inner surface of the outer sheet of the diaper of FIG. 1, illustrating adhesive application patterns in respective bond zones.

The first and second waist elastic elements 36, 37 are secured to the inner and outer sheets 30, 31 with hot melt adhesive applied to a partial or entire circumference of the respective waist elastic elements 36, 37. Referring to FIG. 5, the first and second waist elastic regions 38, 39 in which first and second waist elastic elements 36, 37 are arranged are not coated with hot melt adhesive so that the inner and outer sheets 30, 31 may be bonded to each other with hot melt adhesive applied to the first and second waist elastic elements 36, 37.

The elastic members used for the first and second waist elastic elements 36, 37 are of the same standard and are bonded to the inner and outer sheets 30, 31 under the same standard. In consequence, the spacing dimension between the adjacent second waist elastic elements 37 in the longitudinal direction Y is larger than the spacing dimension between the adjacent first waist elastic elements 36, and therefore the tensile stress in the second waist elastic region 39 is lower than that in the first waist elastic region 38.

In a region between an adjacency of the inner end of the front waist region 13 and an adjacency of the inner end of the rear waist region 15, the inner and outer sheets 30, 31 are bonded to each other with a crotch bond zone 61 defined by a plurality of bonding lines 60 extending in parallel in the transverse direction X. The bonding lines 60 are provided by hot melt adhesive applied in spiral pattern extending in the transverse direction X. A basis mass of the bonding lines 61 is in a range of about 2.0 to about 10.0 g/m² and a spacing dimension (pitch) between the adjacent bonding lines 60 in the longitudinal direction Y is in a range of about 3.5 to about 4.5 mm.

Opposite lateral ends 36a, 36b of the first waist elastic elements 36 are coated with hot melt adhesive in a spiral pattern to define lateral bond zones 63. These lateral bond zones 63 assure that the opposite lateral ends 36a, 36b of the first waist elastic elements 36 are stably fixed to the outer sheet 31 and the first waist elastic elements 36 may be prevented from being peeled off or slipping out from the outer sheet 31 in the course of production process.

Figure 6:
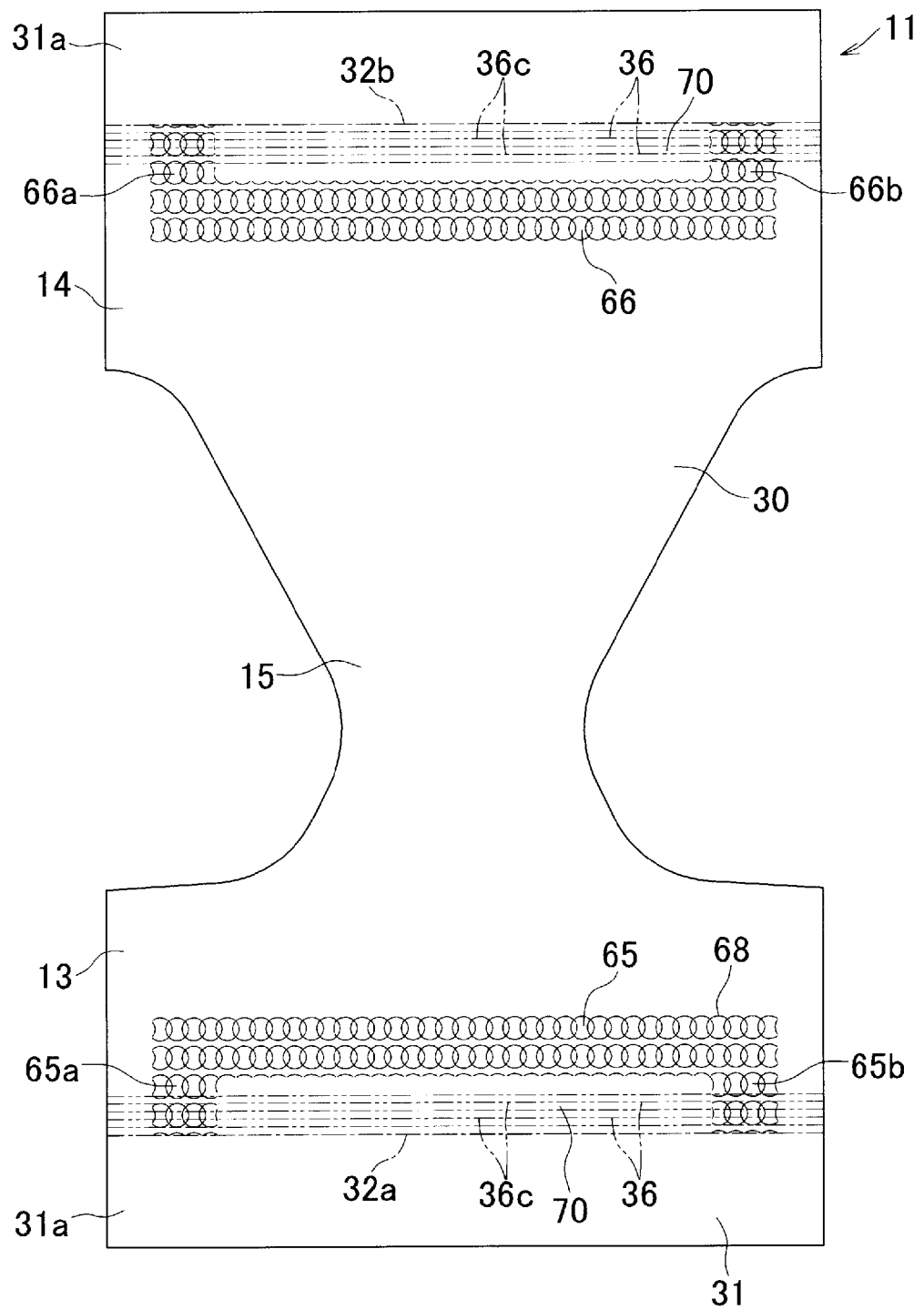
FIG. 6 is a plan view of the chassis of the diaper of FIG. 1 having front and rear flaps developed, illustrating adhesive application patterns in front and rear flaps' bond zones.

Referring to FIG. 6, on the side of the front waist region 13, the non-skin-facing side of the inner sheet 30 is formed with a front flap bond zone 65 having a front middle recess on the outside, i.e., on the side adjacent the front end 16 of the chassis 11. The front middle recess is free of adhesive material. Similarly, on the side of the rear waist region 14, a rear flap bond zone 66 having a rear middle recess on the outside, i.e., on the side adjacent the rear end 17 of the chassis 11, is formed on the non-skin-facing side of the inner sheet 30. The rear middle recess is free of adhesive material. The front and rear flap bond zones 65, 66 respectively have a basis mass in a range of about 3.0 to about 6.0 g/m$^2$ and each defined by two or more bonding lines 68 extending in the transverse direction X and provided by hot melt adhesive applied to the non-skin-facing side of the inner sheet 30 in a spiral pattern. The extensions 31a of the outer sheet extending outward in the longitudinal direction Y beyond the front and rear ends of the inner sheet 30 are folded and bonded to the inner sheet 30 by the front and rear flap bond zones 65, 66 to form the front and rear flaps 33, 34.

Midsections 36c of the first waist elastic elements 36 extend in respective non-bond zones 70 which are located between the respective opposite lateral end portions 65a, 65b; 66a, 66b of the front and rear flap bond zones 65, 66 and which are defined by the respective front and rear middle recesses and, therefore, coated with no hot melt adhesive. The midsections 36c of the first waist elastic elements 36 lying in the non-bond zones 70 of the front and rear flap bond zones 65, 66 are free of direct attachment to the chassis 11. Therefore, the elasticity of at least the midsections 36c of the first waist elastic elements 36 is not affected which assures the first waist elastic elements 36 to provide a desired tensile stress to be described below.

Figure 7:
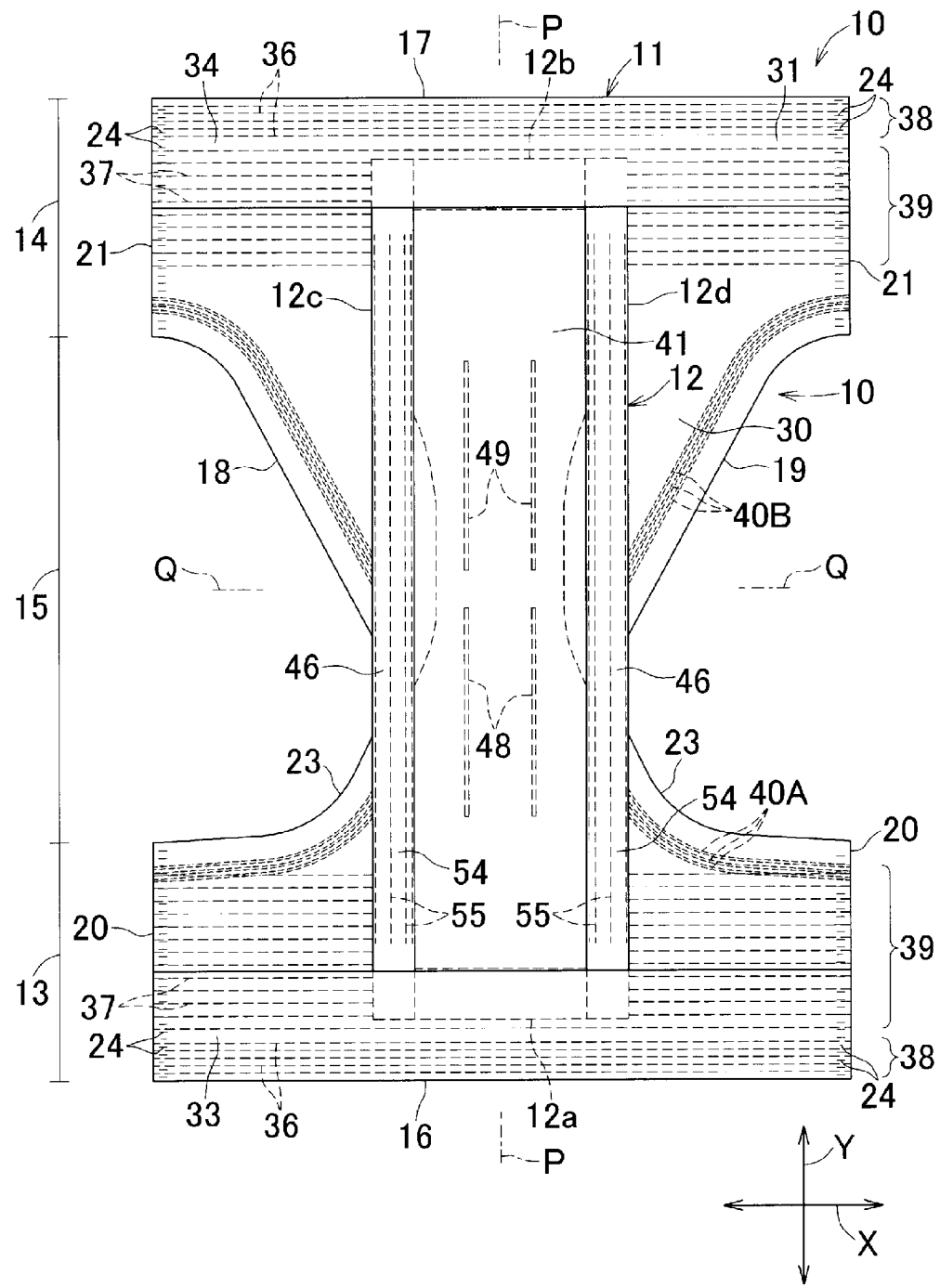
FIG. 7 is a partially cutaway unfolded plan view of the diaper showing another exemplary embodiment of the diaper.

Referring to FIG. 7, the front and rear leg elements 40A, 40B are formed of flat rubber bands, for example, flat rubber bands each having a width dimension of about 1.6 mm and a stretch ratio in a range of about 1.0 to about 2.0. The front and rear leg elastic elements 40A, 40B may be equal or different in number, but when such numbers are equal, it is preferred that a stretch ratio of the rear leg elastic elements 40B should be higher than that of the front leg elastic elements 40A so that entire of crotch region 15 may fit to the wearer's body and movements of the wearer's thighs could not be obstructed. In this case, for example, the stretch ratio of the front leg elastic elements 40A may be in a range of about 1.6 to about 1.8 and the stretch ratio of the rear leg elastic elements 40B may be in a rage of about 2.0 to about 2.2. When the front and rear leg elastic elements are formed of flat rubber bands, an area over which the flat rubber bands are put in contact with the wearer's thighs as well as it allows surely to prevent urine from sideway-leaking without pressure traces on the wearer's skin even if the flat rubber bands have a relative high tensile stress. Therefore, the diaper 10 according to this embodiment can assure a soft texture in the first and second waist elastic regions 38, 39 provided with the first and second elastic members formed of one or more threads, strands or string elastics as well as in the leg-openings of the crotch region 15, it could prevent urine from sideway-leaking without pressure on the wearer's skin.

<Measurement of Tensile Stress of the First Waist Elastic Regions 38>

The following TABLE 1 includes measurement results of tensile stress of the respective first waist elastic regions (the waist-opening's periphery of the diaper) 38 in Examples 1-2 and tensile stress of the corresponding regions in the diapers of Comparative Examples 1-4.

TABLE 1

|  | 1st cycle 255% stretched state | 2nd cycle 167% stretched state | Easiness for expanding waist opening periphery to wear article | Stability of waist region of article on wearer's body |
|---|---|---|---|---|
| Example 1 | 5.8 | 1.7 | good | good |
| Example 2 | 5.9 | 2.1 | good | good |
| Comparative Example 1 | 6.6 | 1.8 | poor | good |
| Comparative Example 2 | 9.7 | 2.8 | poor | good |
| Comparative Example 3 | 8.4 | 2.2 | poor | good |
| Comparative Example 4 | 4.7 | 1.4 | good | poor |

(unit: N/35 mm)

The disposable diapers according to Examples 1 and 2 respectively had the basic construction of the diaper 10 as described herein, and the disposable diapers according to Comparative Examples 1 through 4 were of the pants-type respectively consisting of a liquid-absorbent structure and a chassis.

Example 1

A spunbond nonwoven fabric having a basis mass of about 17 g/m$^2$ was used as the outer sheet 31, an SMS nonwoven fabric having a basis mass of about 15 g/m$^2$ was used as the inner sheet 30, and five elastic threads, specifically, LYCRA 940DTEX manufactured by TORAY OPERLONTEX CO., LTD., arranged at a pitch of about 6.0 mm and attached while being stretched at a stretch ratio of about 3.0 in the transverse direction X between the inner and outer sheets 30, 31 were used as the respective first waist elastic elements 36.

Example 2

Example 2 was similar to Example 1, except for the first waist elastic elements 36. Specifically, six elastic threads, specifically, LYCRA 940DTEX manufactured by TORAY OPERLONTEX CO., LTD., arranged at a pitch of about 6.0 mm and attached while being stretched at a stretch ratio of about 2.7 in the transverse direction X between the inner and outer sheets 30, 31 were used as the respective first waist elastic elements 36.

Comparative Example 1

The outer sheet was a spunbond nonwoven fabric having a basis mass of about 17 g/m$^2$, the inner sheet was an SMS nonwoven fabric having a basis mass of about 15 g/m$^2$, and the respective waist elastic elements corresponding to the respective first waist elastic elements 36 included five flat rubber elements, specifically, JPW-WG-AW flat rubber elements manufactured by Saha-Union Corporation, arranged at a pitch of about 6.0 mm and attached while being stretched at a stretch ratio of about 3.0 in the transverse direction of the diaper.

Comparative Example 2

The outer sheet was an air-through nonwoven fabric having a basis mass of about 17 g/m², the inner sheet was a spunbond nonwoven fabric having a basis mass of about 20 g/m², and the respective waist elastic elements corresponding to the respective waist elastic elements 36 included six flat rubber elements made of natural rubber having a width dimension of about 2.5 mm arranged at a pitch of about 5.0 mm and attached while being stretched at a stretch ratio of about 3.0 in the transverse direction of the diaper.

Comparative Example 3

The outer sheet was an air-through nonwoven fabric having a basis mass of about 24 g/m², the inner sheet was a spunbond nonwoven fabric having a basis mass of about 21 g/m², and the respective waist elastic elements corresponding to the respective waist elastic elements 36 included eight flat rubber elements made of natural rubber having a width dimension of about 0.1 mm arranged at a pitch of about 3.0 mm and attached while being stretched at a stretch ratio of about 2.8 in the transverse direction of the diaper.

Comparative Example 4

The outer sheet was a spunbond nonwoven fabric having a basis mass of about 17 g/m², the inner sheet was an SMS nonwoven fabric having a basis mass of about 15 g/m², and the respective waist elastic elements corresponding to the respective first waist elastic elements 36 included five flat rubber elements, specifically, LYCRA 940DTEX manufactured by TORAY OPERLONTEX CO., LTD. arranged at a pitch of about 6.0 mm and attached while being stretched at a stretch ratio of about 2.5 in the transverse direction X.

The waist elastic elements in the diapers according to the Comparative Examples were different from the first waist elastic elements 36 in that the elastic elements in the Comparative Examples were secured between the inner and outer sheets with hot melt adhesive applied to the entire area of these elastic elements in a planar pattern or in a spiral pattern.

<Measuring Method for Tensile Stress>

Figure 8:
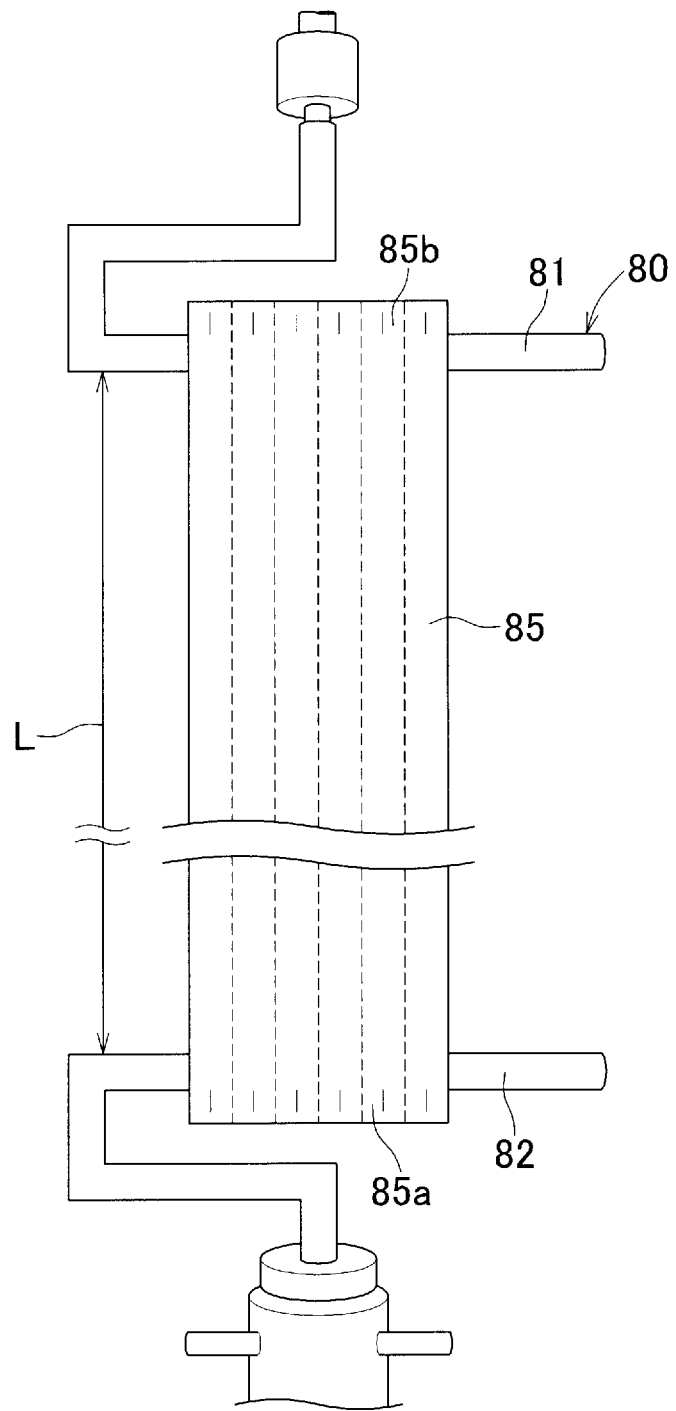
FIG. 8 is a diagram schematically illustrating a process of measuring tensile stress of test pieces taken out from the respective examples of the diaper of FIG. 1.

Referring to FIG. 8, tensile stress values of the waist-opening peripheries (the first waist elastic zones (regions) 38 in Examples 1 and 2) in the respective diapers were measured using Tensile Tester 80 manufactured by Instron Japan Co., Ltd. (INSTRON Model: 5564) in accordance with a method as described below. In Tensile Tester 80, clamps for upper and lower chucks are previously detached, thin rod-like upper and lower jigs 81, 82 are attached to the respective chucks and a spacing dimension L between the upper and lower jigs is set to a length dimension of the diaper in the transverse direction X in its non-stretched state. An electric power switch for the Tensile Tester 80 is turned on 30 minutes before the measurement is started and the measurement is carried on under conditions of a cycle mode (two cycles) and a tension rate of 300 mm/min.

First, standard M-sized diapers (with a length-dimension of the waist line in its non-stretched state of about 360 mm) were prepared, Each diaper was cut along a line at a distance of about 35 mm from the periphery of the waist opening, to obtain an annular measurement sample 85 which was about 35 mm wide. The "about 35 mm" distance corresponds to a length dimension in the longitudinal direction of respective regions over which the last joints of the wearer's or care person's thumbs are placed to expand the waist-opening in the circumferential direction. In Examples 1 and 2, these regions were the first waist elastic zones 38 and, in the Comparative Examples 1 through 4, these regions were the waist-opening peripheries provided with the waist elastic elements corresponding to the first waist elastic zones 38.

Then, one lateral end portion 85a (corresponding to the side seams 24 on e.g., the left side, in FIGS. 1-2) of the annular measurement sample 85 cut off from each of the diapers was put on a midsection of the lower jig 82. The sample 85 was pulled upward with the lower jig 82 being held in contact with the lateral end portion 85a to put the other lateral end portion 86b (corresponding to the side seams 24 on e.g., the right side, in FIGS. 1-2) on a midsection of the upper jig 81. From this state, the upper and lower jig 81, 82 were moved relative to each other in the vertical direction (corresponding to the transverse direction X) until the waist elastic elements in the sample 85 became substantially straight which indicated a "non-stretched state" of the sample 85.

The initial spacing dimension L between the upper and lower jigs 81, 82 at which the measurement sample 85 was considered to be in the non-stretched state was set to 100%. In the non-stretched state, the measurement sample 85 was maintained under an appropriate tension. From such an initial, non-stretched state, the upper and lower jigs 81, 82 were moved away from each other (at a tension rate of 300 mm/min) to stretch the measurement sample 85 until the spacing dimension L increased to about 255% (i.e., 255% elongation) and tensile stress (N/35 mm) at this moment was measured (first cycle). Then, the measurement sample 85 having been stretched to about 255% in this manner was allowed to gradually contract (by moving the upper and lower jigs 81, 82 toward each other) until the spacing dimension L between the upper and lower jigs 81, 82 was reduced to about 167% (i.e., 167% elongation) whereupon tensile stress (N/35 mm) was measured again (second cycle).

In the standard M-size diaper applicable to the wearer's waist width dimension in a range of 600 to 850 mm and the wearer's waist circumferential length dimension in the non-stretched state of about 360 mm, the waist circumferential length dimension in its about 255% stretched state (i.e., at 255% elongation) is about 920 mm. In the standard L-size diaper applicable to the wearer's waist width dimension in a range of 750 to 1000 mm and the wearer's waist circumferential length dimension in its non-stretched state of about 420 mm, the waist circumferential length dimension in its about 255% stretched state is about 1070 mm. The "255% stretched state" generally corresponds to the maximum dimension that the wearer or the care personnel may stretch the waist-opening in order to put on the diaper. The "167% stretched state" generally corresponds to a stretched state when the diaper is being normally worn on the wearer's body.

The criteria "easiness for expanding waist-opening periphery to wear article" and "stability of waist region of article on wearer's body" in TABLE 1 were evaluated by a total of ten test subjects (5 males and 5 females) aged 70 to 90 wearing adult diapers. Specifically, the easiness for stretching the waist circumferential dimension to about 255% elongation to widen the waist-opening periphery (for putting the diaper on) and the stability of the diaper's waist region on the wearer's body 3 hours after the diaper had been put on the wearer's body were evaluated.

In the respective evaluations for "easiness for expanding waist-opening periphery to wear article", the word "good" means that the subject was able to stretch the waist-opening periphery by moderately pulling the waist-opening periphery in the transverse direction to put the diaper on, and felt no noticeable displacement of the diaper's waist region during use of the diaper. The word "poor" means that the subject had to pull the waist-opening periphery in the transverse direction with a relatively strong force to widen the waist-opening to a desired size to put the diaper on, and felt a noticeable displacement of the diaper's waist region during use of the diaper.

With respect to "stability of waist region of article on wearer's body", similar evaluations were obtained from a test of the stability of the diaper's waist region on the wearer's body during the movement of the wearer. Specifically, it was tested whether the diaper's waist region was noticeably displaced or not during 15 repeated movements up and down a stepstool after walking for 1 minute (active movement). This test conducted 3 hours after the diaper had been put on the wearer's body.

A "noticeable displacement" of the diaper's waist region both during normal wear and during active movement was indicated when the diaper's waist region had been displaced by about 15 mm or more from its initial position in the longitudinal direction (immediately after the diaper was put on the wearer's body).

For each criterion, the Example or Comparative Example was determined as "good" (or "poor") when of the 10 test subjects evaluated it as "good" (or "poor").

In Examples 1 and 2, as will be apparent from the result indicated by TABLE 1, the tensile stress values at 255% stretching (i.e., at 255% elongation) were about 6.0N or lower and the evaluation of "easiness for expanding waist-opening periphery to wear article" was "good". The tensile stress values at 167% stretching (i.e., at 167% elongation) were 1.7N and 2.1N, respectively, and the evaluation of "stability of waist region of article on wearer's body" was also "good".

In Comparative Examples 1 through 3, the tensile stress values at 255% stretching were higher than 6.0N and the evaluation of "easiness for expanding waist-opening periphery to wear article" was "poor". The tensile stress values at 167% stretching were higher than 1.7N and the evaluation of "stability of waist region of article on wearer's body" was also "good". In Comparative Example 4, the tensile stress value at 255% stretching was 4.7N and the evaluation of "easiness for expanding waist-opening periphery to wear article" was "good". In contrast, the tensile stress value at 167% stretching was 1.4N and the evaluation of "stability of waist region of article on wearer's body" was "poor".

Such measurement results indicate that, in Examples 1 and 2, the tensile stress at 255% stretching of the respective measurement samples 85 from the non-stretched state thereof may be set to a range of about 4.5 to about 6.0N/35 mm, and the tensile stress at 167% stretching of the respective measurement samples 85 may be set to about 1.5N/35 mm or higher, more preferably, to a range of about 1.7 to 2.1N/35 mm, to obtain the evaluation "good" for "easiness for expanding waist-opening periphery to wear article" as well as for "stability of waist region of article on wearer's body". It should be noted here that the diaper 10 according to embodiments of this invention is the diaper for an adult, particularly, for an aged person having relative poor muscular strength and if the force required to widen the waist-opening to wear the diaper is higher than 6.0N, it may be difficult for such wearer to widen the waist-opening and/or the wearer's foot might be caught by the waist-opening periphery and/or the wearer may tip over in the course of putting the diaper on his or her body. Being different from a disposable diaper for a baby who constantly moves his or her body, in the disposable diaper for an adult, particularly for an aged person, the waist-opening tensile stress should be set to be relatively low to assist the wearer during the course of putting the diaper on his or her body. However, if the tensile stress is set to about 1.4N or lower, the diaper's waist region might be displaced during use of the diaper and, in consequence, cause sideway-leakage of body waste.

Tensile stress may depend on various factors such as the kinds of the fibrous nonwoven fabric used for the inner and outer sheets constituting the chassis, basis masses thereof, the number, fineness, arranging pitches of the waist elastic elements, coating patterns of adhesive used to bond these components and basis masses of adhesive etc. As the most important factors that result in the desired tensile stress, it is noticed that Examples 1 and 2 used the elastic threads having relatively small fineness of about 940 dtex while Comparative Examples 1 through 3 use flat rubber elements having a significant width dimension. In addition, it should also be noticed that, in Examples 1 and 2, the front and rear flap bond zones 65, 66 serving to fix the front and rear flaps 33, 34 defined by fold lines 31a of the outer sheet 31 were shaped to be concave outward in the longitudinal direction Y.

Figure 9:
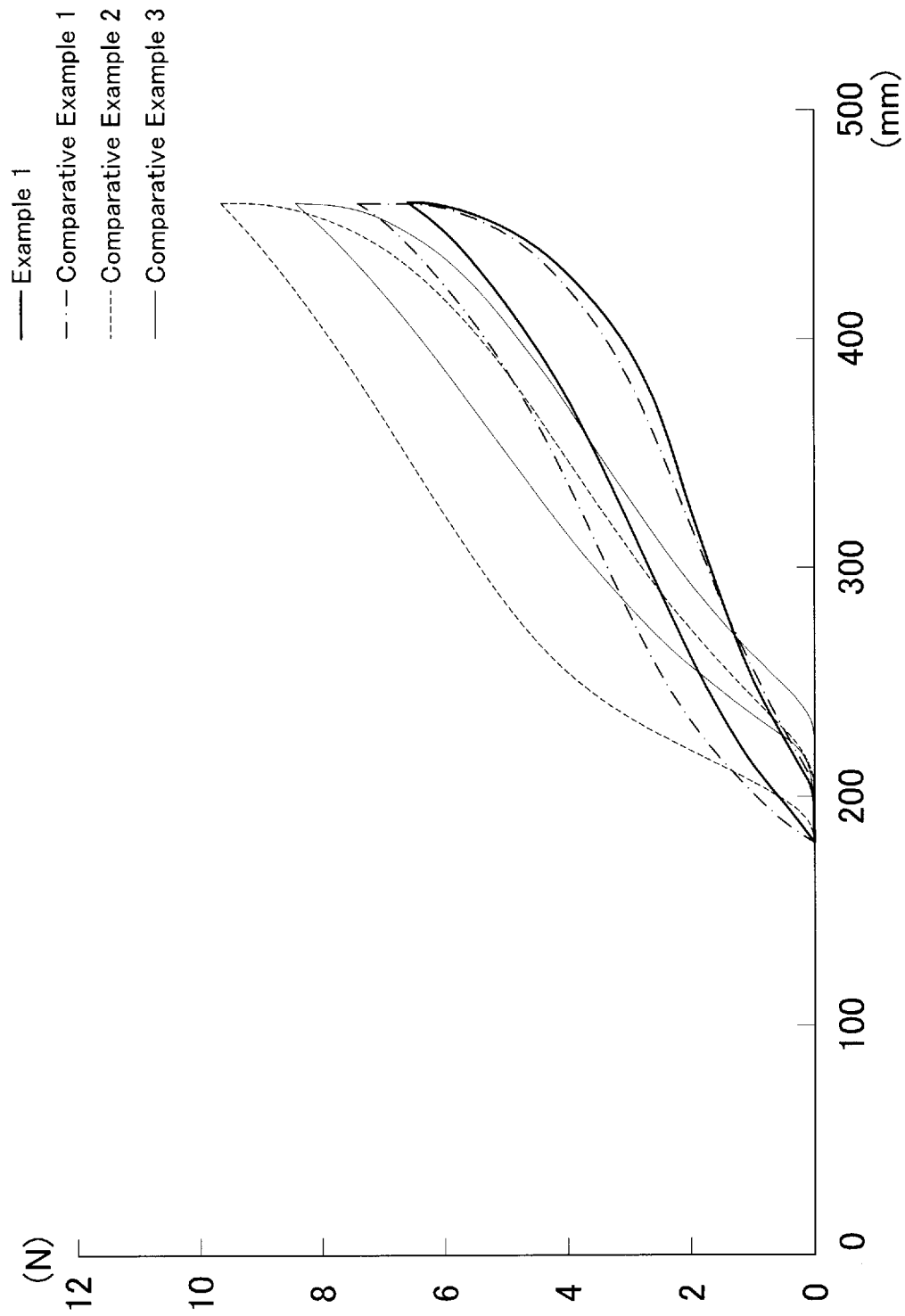
FIG. 9 is a graphic diagram indicating a measurement result of the tensile stress values of the respective test pieces of the diaper of FIG. 1.

FIG. 9 is a graphic diagram illustrating relationships between stretched dimensions of the measurement samples 85 of Examples 1 and Comparative Examples 1 through 3 and values of the tensile stress at the stretched dimensions. The abscissa axis in FIG. 9 represents respective halves of the waist circumferential length dimensions (mm) (about 180 mm corresponding to one halve of the waist circumferential dimension in its non-stretched state) measured as the measurement samples 85 were pulled in the transverse direction, and the ordinate axis represents the tensile stress values (N) of the measurement samples 85 having been stretched to the respective length dimensions thereof.

Referring to FIG. 9, the graphic diagram representing measurement results of the tensile stress values obtained from the respective measurement samples 85 indicate respective tensile stress-elongation curves including hystereses such that the tensile stress, at the same degree of elongation, is lower when the respective measurement samples 85 were released from the tensile force to contract (second cycle) than when the respective measurement samples 85 were pulled in the transverse direction to be stretched (first cycle). As will be apparent from FIG. 9, the tensile stress of Example 1 in the first cycle is lower than those of Comparative Examples 1 through 3 in the first cycle, but is at least similar to that of Comparative Example 1 in the second cycle. Consequently, in comparison to the diapers of Comparative Examples 1 through 3, the diaper 10 of Example 1 makes it possible to widen the waist-opening with a relatively small force and stably fits to the wearer's waist without causing the diaper's waist region to be slipped down during use of the diaper.

While various types of adhesive of known art or to be developed may be used without limitation for the respective bond zones, the hot melt adhesive particularly to be used for the crotch bond zone 61 as well as for the front and rear flap bond zones 65, 66 is preferably selected, for example, from a group of rubber-based adhesives such as an SBS (styrene/butadiene/styrene)-based adhesive and an SIS (styrene/isoprene/styrene)-based adhesive in order that the elasticity of the first and second waist elastic elements 36, 37 can be protected against affection of the adhesive as reliably as possible.

The component members of the diaper 10 are not limited to those specifically described in this specification but the other various types of material widely used or to be developed in the relevant technical field may be used without limitation. The terms "first" and "second" used herein are used merely to distinguish the similar elements, similar positions or other similar means.

As has previously been described, the disposable wearing articles according to embodiments of this invention target adult users, particularly, aged persons. Such disposable wearing articles are not limited to disposable diapers, and also include incontinent pants and the like. The disposable wearing articles according to embodiments of this invention are based on creative intention and intended use described below.

New functions other than the basic functions, for example, preventive functions against stuffiness within the disposable diaper, leakage of bodily fluids and wearer's skin rash, are provided for disposable diapers, particularly for adult diapers. Specifically, such new functions include comfortable texture comparable to underwear, compatibility with the movement of the wearer's body, and handiness allowing the wearer to put on the diaper by the wearer's own physical ability. Particularly in disposable diapers for adults, the requirement is different from disposable diapers for babies or children in that the wearer is expected to handle (e.g., wear) the diaper by him- or herself and therefore its handiness is an important issue. It is not rare that an aged person could not put on a diaper without hands of a care personnel or helper. Considering this situation, the creative intention and the intended use of the article according to embodiments of this invention are to enable self-reliance support for aged persons and those who require nursing care, at least with respect to body waste disposal. Specifically, the article, e.g., diaper, in accordance with embodiments of this invention is configured so that an aged person can him- or herself handle the diaper to put it on his or her body and make use of the diaper without anxiety. In this way, the article according to embodiments of this invention is configured to support self-reliance of aged persons and/or those who require nursing care with respect to body waste disposal, to make such persons keep their self-respect and to provide dynamic life style. The article according to embodiments of this invention was developed as a tool for solving various problems occurring in the field of social welfare and nursing care as the population of aged persons increases and this article is believed to be socially useful. The article according to embodiments of this invention has a clear distinction from baby diapers, and a unique construction to realize the intended use and creative intention described above.

The aspect(s) of the present invention described above may be arranged in at least the following items:

(i) A disposable wearing article having a longitudinal direction and a transverse direction being orthogonal to the longitudinal direction, including a chassis having a skin-facing side, a non-skin-facing side, a front waist region, a rear waist region and a crotch region extending between the front and rear waist regions, and a liquid-absorbent structure extending across the crotch region into the front and rear waist regions, wherein:

the chassis has an inner sheet lying on the skin-facing side and an outer sheet lying on the non-skin-facing side;

the article further comprises waist elastic elements sandwiched between the inner and outer sheets to extend along a waist-opening periphery of the chassis in the transverse direction;

the waist elastic elements are bonded to the chassis while being stretched in the transverse direction at a stretch ratio in a range of about 2.5 to about 3.0 and have fineness in a range of about 800 to about 1000 dtex;

a spacing dimension between the waist elastic elements adjacent in the longitudinal direction is in a range of about 5.5 to about 6.0 mm; and an annular waist elastic region in which the waist elastic elements are present has a tensile stress at 255% elongation in the transverse direction in a range of about 4.5 to about 6.0N/35 mm and a tensile stress at 167% elongation in the transverse direction in a range of about 1.7 to about 2.1N/35 mm.

The aspect described in the above item (i) may include at least the following embodiments:

(ii) The inner sheet is formed of an spunbond-meltblown-spunbond (SMS) fibrous nonwoven fabric having a basis mass in a range of about 10 to about 25 g/m$^2$, the outer sheet is formed of a spunbond nonwoven fabric having a basis mass in a range of about 15 to about 25 g/m$^2$, and the waist elastic elements are secured between the inner and outer sheets with hot melt adhesive applied to a partial or entire peripheral surfaces of the waist elastic elements.

(iii) The waist elastic elements include:

first waist elastic elements extending along the waist-opening periphery in the transverse direction; and second waist elastic elements positioned between the first waist elastic elements and the crotch region in a such a manner that a spacing dimension between the second waist elastic elements adjacent in the longitudinal direction is larger than a spacing dimension between the first waist elastic elements adjacent in the longitudinal direction, and a first waist elastic region in which the first waist elastic elements are present has a tensile stress higher than a tensile stress of a second waist elastic regions in which the second waist elastic elements are present.

(iv) The outer sheet has extensions extending outward in the longitudinal direction beyond front and rear ends of the inner sheet, the extensions being folded inward along the front and rear ends of the inner sheet and bonded to the inner sheet via front and rear flap bond zones defined on the skin-facing side of the inner sheet to form front and rear flaps.

(v) The front and rear flap bond zones each have a middle recess on an outside thereof, the middle recesses being free of adhesive material, and midsections of the waist elastic elements extend in non-bond zones which extend in the transverse direction between respective opposite lateral end portions of the front and rear flap bond zones and which are defined by the middle recesses of the front and rear flap bond zones.

(vi) A zone of the crotch region closer to the front waist region are provided along front half peripheral edges of the respective leg-openings with front leg elastic elements extending convexly inward and a zone of the crotch region closer to the rear waist region are provided along rear half peripheral edges of the respective leg-openings with rear leg elastic elements extending convexly inward, and the front and rear leg elastic elements are formed of flat rubber bands.

Alternatively, the aspect(s) of the present invention may be arranged in at least the following items:

(vii) A disposable wearing article having a longitudinal direction and a transverse direction being orthogonal to the longitudinal direction, including a chassis having a skin-facing side, a non-skin-facing side, a front waist region, a rear waist region and a crotch region extending between the front and rear waist regions, and a liquid-absorbent structure on the skin-facing side of the chassis, wherein:

the chassis has an inner sheet lying on the skin-facing side and an outer sheet lying on the non-skin-facing side;

the article further comprises waist elastic elements sandwiched between the inner and outer sheets to extend along a waist-opening periphery of the chassis in the transverse direction;

the waist elastic elements are bonded to the chassis while being stretched in the transverse direction at a stretch ratio in a range of about 2.5 to about 3.0 and have fineness in a range of about 800 to about 1000 dtex; and an annular waist elastic region, which has a width of 35 mm from the waist opening periphery and in which the waist elastic elements are present, exhibits a tensile stress at 255% elongation in the transverse direction in a range of 4.5 to 6.0N/35 mm and a tensile stress at 167% elongation in the transverse direction in a range of about 1.5N/35 mm or higher.

The aspect described in the above item (vi) may include at least the following embodiments:

(viii) The inner sheet is formed of an spunbond-meltblown-spunbond (SMS) fibrous nonwoven fabric having a basis mass in a range of about 10 to about 25 g/m$^2$, the outer sheet is formed of a spunbond nonwoven fabric having a basis mass in a range of about 15 to about 25 g/m$^2$, and the waist elastic elements are secured between the inner and outer sheets with hot melt adhesive applied to a partial or entire peripheral surfaces of the waist elastic elements.

(ix) The waist elastic elements include:

first waist elastic elements extending along the waist-opening periphery in the transverse direction; and second waist elastic elements positioned between the first waist elastic elements and the crotch region in a such a manner that a spacing dimension between the second waist elastic elements adjacent in the longitudinal direction is larger than a spacing dimension between the first waist elastic elements adjacent in the longitudinal direction, and a first waist elastic region in which the first waist elastic elements are present has a tensile stress higher than a tensile stress of a second waist elastic regions in which the second waist elastic elements are present.

(x) The outer sheet has extensions extending outward in the longitudinal direction beyond front and rear ends of the inner sheet, the extensions being folded inward along the front and rear ends of the inner sheet and bonded to the inner sheet via front and rear flap bond zones defined on the skin-facing side of the inner sheet to form front and rear flaps.

(xii) The front and rear flap bond zones each have a middle recess on an outside thereof, the middle recesses being free of adhesive material, and midsections of the waist elastic elements extend in non-bond zones which extend in the transverse direction between respective opposite lateral end portions of the front and rear flap bond zones and which are defined by the middle recesses of the front and rear flap bond zones.

The described items and/or embodiments provide one or more of the following effects.

The waist elastic regions (first waist elastic regions) have a tensile stress at 255% elongation in the transverse direction is as low as in a range of about 4.5 to about 6.0N/35 mm. Therefore, even an aged person whose muscular strength is relatively weak is likely able to put the wearing article on the aged person's body by the person's own ability without being aided by a care personnel. The tensile stress at 167% elongation in the transverse direction is as sufficiently high as in a range of about 1.7 to about 2.1N/35 mm. Consequently, the waist region of the wearing article is unlikely to slip down during use of the article and sideway-leakage of body waste is unlikely to occur. In contrast with the case in which elastic elements such as flat rubber bands are used for the waist elastic elements, the area over which the waist elastic elements press the wearer's skin is sufficiently small to prevent these elastic elements from compressing the wearer's abdominal region and, in addition, not to create a feeling of discomfort against the wearer.

This application claims the benefit of Japanese Application Nos. 2011-043367 and 2012-40762 the entire disclosures of which are incorporated by reference herein.

The invention claimed is:

1. A disposable wearing article having a longitudinal direction and a transverse direction being orthogonal to the longitudinal direction, comprising a chassis having a skin-facing side, a non-skin-facing side, a front waist region, a rear waist region and a crotch region extending between the front and rear waist regions, and a liquid-absorbent structure extending across the crotch region into the front and rear waist regions, wherein:

the chassis has an inner sheet lying on the skin-facing side and an outer sheet lying on the non-skin-facing side;

the article further comprises waist elastic elements sandwiched between the inner and outer sheets to extend along a waist-opening periphery of the chassis in the transverse direction;

the waist elastic elements are bonded to the chassis while being stretched in the transverse direction at a stretch ratio in a range of about 2.5 to about 3.0 and have fineness in a range of about 800 to about 1000 dtex;

a spacing dimension between the waist elastic elements adjacent in the longitudinal direction is in a range of about 5.5 to about 6.0 mm; and an annular waist elastic region in which the waist elastic elements are present has a tensile stress at 255% elongation in the transverse direction in a range of about 4.5 to about 6.0N/35 mm and a tensile stress at 167% elongation in the transverse direction in a range of about 1.7 to about 2.1N/35 mm.

2. The wearing article defined by claim 1, wherein the inner sheet is formed of an spunbond-meltblown-spunbond (SMS) fibrous nonwoven fabric having a basis mass in a range of about 10 to about 25 g/m$^2$, the outer sheet is formed of a spunbond nonwoven fabric having a basis mass in a range of about 15 to about 25 g/m$^2$, and the waist elastic elements are secured between the inner and outer sheets with hot melt adhesive applied to a partial or entire peripheral surfaces of the waist elastic elements.

3. The wearing article defined by claim 1, wherein the waist elastic elements include:

first waist elastic elements extending along the waist-opening periphery in the transverse direction; and second waist elastic elements positioned between the first waist elastic elements and the crotch region in a such a manner that a spacing dimension between the second waist elastic elements adjacent in the longitudinal direction is larger than a spacing dimension between the first waist elastic elements adjacent in the longitudinal direction, and a first waist elastic region in which the first waist elastic elements are present has a tensile stress higher than a tensile stress of a second waist elastic regions in which the second waist elastic elements are present.

4. The wearing article defined by claim 1, wherein the outer sheet has extensions extending outward in the longitudinal direction beyond front and rear ends of the inner sheet, the extensions being folded inward along the front and rear ends of the inner sheet and bonded to the inner sheet via front and rear flap bond zones defined on the skin-facing side of the inner sheet to form front and rear flaps.

5. The wearing article defined by claim 4, wherein
the front and rear flap bond zones each have a middle recess on an outside thereof, the middle recesses being free of adhesive material, and
midsections of the waist elastic elements extend in non-bond zones which extend in the transverse direction between respective opposite lateral end portions of the front and rear flap bond zones and which are defined by the middle recesses of the front and rear flap bond zones.

6. The wearing article defined by claim 1, a zone of the crotch region closer to the front waist region are provided along front half peripheral edges of the respective leg-openings with front leg elastic elements extending convexly inward and
a zone of the crotch region closer to the rear waist region are provided along rear half peripheral edges of the respective leg-openings with rear leg elastic elements extending convexly inward, and the front and rear leg elastic elements are formed of flat rubber bands.

7. A disposable wearing article having a longitudinal direction and a transverse direction being orthogonal to the longitudinal direction, comprising
a chassis having a skin-facing side, a non-skin-facing side, a front waist region, a rear waist region and a crotch region extending between the front and rear waist regions, and
a liquid-absorbent structure on the skin-facing side of the chassis,
wherein:
the chassis has an inner sheet lying on the skin-facing side and an outer sheet lying on the non-skin-facing side;
the article further comprises waist elastic elements sandwiched between the inner and outer sheets to extend along a waist-opening periphery of the chassis in the transverse direction;
the waist elastic elements are bonded to the chassis while being stretched in the transverse direction at a stretch ratio in a range of about 2.5 to about 3.0 and have fineness in a range of about 800 to about 1000 dtex; and
an annular waist elastic region, which has a width of 35 mm from the waist opening periphery and in which the waist elastic elements are present, exhibits a tensile stress at 255% elongation in the transverse direction in a range of about 4.5 to about 6.0N/35 mm and a tensile stress at 167% elongation in the transverse direction in a range of about 1.5N/35 mm or higher.

8. The wearing article defined by claim 7, wherein the inner sheet is formed of an spunbond-meltblown-spunbond (SMS) fibrous nonwoven fabric having a basis mass in a range of about 10 to about 25 g/m$^2$, the outer sheet is formed of a spunbond nonwoven fabric having a basis mass in a range of about 15 to about 25 g/m$^2$, and the waist elastic elements are secured between the inner and outer sheets with hot melt adhesive applied to a partial or entire peripheral surfaces of the waist elastic elements.

9. The wearing article defined by claim 7, wherein the waist elastic elements include
first waist elastic elements extending along the waist-opening periphery in the transverse direction, and
second waist elastic elements positioned between the first waist elastic elements and the crotch region in a such a manner that a spacing dimension between the second waist elastic elements adjacent in the longitudinal direction is larger than a spacing dimension between the first waist elastic elements adjacent in the longitudinal direction, and a first waist elastic region in which the first waist elastic elements are present has a tensile stress higher than a tensile stress of a second waist elastic regions in which the second waist elastic elements are present.

10. The wearing article defined by claim 7, wherein the outer sheet has extensions extending outward in the longitudinal direction beyond front and rear ends of the inner sheet, the extensions being folded inward along the front and rear ends of the inner sheet and bonded to the inner sheet via front and rear flap bond zones defined on the skin-facing side of the inner sheet to form front and rear flaps.

11. The wearing article defined by claim 10, wherein
the front and rear flap bond zones each have a middle recess on an outside thereof, the middle recesses being free of adhesive material, and
midsections of the waist elastic elements extend in non-bond zones which extend in the transverse direction between respective opposite lateral end portions of the front and rear flap bond zones and which are defined by the middle recesses of the front and rear flap bond zones.

* * * * *